US009354225B2

(12) United States Patent
Lizano-González et al.

(10) Patent No.: US 9,354,225 B2
(45) Date of Patent: May 31, 2016

(54) DETECTION OF ANALYTES PRESENT IN EXOSOMES

(75) Inventors: Sergio Agustin Lizano-González, Cape Elizabeth, ME (US); Lisa Ann Estey, Westbrook, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 1479 days.

(21) Appl. No.: 12/613,087

(22) Filed: Nov. 5, 2009

(65) Prior Publication Data

US 2011/0104720 A1 May 5, 2011

(51) Int. Cl.
*G01N 33/50* (2006.01)

(52) U.S. Cl.
CPC ...... *G01N 33/5076* (2013.01); *G01N 2333/916* (2013.01); *G01N 2800/2828* (2013.01)

(58) Field of Classification Search
None
See application file for complete search history.

(56) References Cited

U.S. PATENT DOCUMENTS 6,620,629 B1 * 9/2003 Prusiner et al. ............... 436/543

OTHER PUBLICATIONS

Zha et al. Sphingomyelinase Treatment Induces ATP-independent Endocytosis . J Cell Biol. Jan. 12, 1998;140(1):39-47.*
Trajkovic et al. Ceramide Triggers Budding of Exosome Vesicles into Multivesicular Endosomes. 2008. Science. Feb. 29, 2008;319(5867)1244-7.*
Marsh, et al., "No ESCRTs for Exosomes", Science, vol. 319, p. 1191-1192 (2008).
Trajkovic, et al., "Ceramide Triggers Budding of Exosome Vesicles into Multivesicular Endosomes", Science, vol. 319, p. 1244-1247 (2008).
Porto-Carreiro, et al., "Prions and exosomes: From PrPc trafficking to PrPsc propagation", Blood Cells, Molecules and Diseases, vol. 35, p. 143-148 (2005).
Liu, et al., "Inhibition of the Neutral Magnesium-dependent Sphingomyelinase by Glutathione", The Journal of Biological Chemistry, vol. 272, No. 26, p. 16281-16287 (1997).
Fevier, et al., "Cells release prions in association with exosomes", PNAS, vol. 101, No. 26, p. 9683-9688 (2004).
Liu, et al., "Glutathione Regulation of Neutral Sphingomyelinase in Tumor Necrosis Factor-a-induced Cell Death", The Journal of Biological Chemistry, vol. 273, No. 18, p. 11313-11320 (1998).

* cited by examiner

*Primary Examiner* — Michelle S Horning
(74) *Attorney, Agent, or Firm* — McDonnell, Boehnen, Hulbert & Berghoff, LLP

(57) ABSTRACT

The invention provides methods for detection in stored biological samples of PrPsc and other analytes that are present in exosomes.

15 Claims, 5 Drawing Sheets

A

B

| | UNTREATED | | | | |
|---|---|---|---|---|---|
| | OD 1 | OD 2 | AVE | SD | % |
| <1H | 0.144 | 0.134 | 0.139 | 0.007 | 100 |
| 24H RT | 0.079 | 0.082 | 0.081 | 0.002 | **58** |
| 24H 4°C | 0.064 | 0.062 | 0.063 | 0.001 | **45** |
| | L-GLUTATHIONE (REDUCED) 5mM | | | | |
| | OD 1 | OD 2 | AVE | SD | % |
| <1H | 0.148 | 0.131 | 0.140 | 0.012 | 100 |
| 24H RT | 0.141 | 0.133 | 0.137 | 0.006 | 98 |
| 24H 4°C | 0.128 | 0.148 | 0.138 | 0.014 | 99 |
| | EGTA (5mM) | | | | |
| | OD 1 | OD 2 | AVE | SD | % |
| <1H | 0.102 | 0.105 | 0.104 | 0.002 | 100 |
| 24H RT | 0.103 | 0.12 | 0.112 | 0.012 | 107 |
| 24H 4°C | 0.109 | 0.116 | 0.113 | 0.005 | 108 |

A

B

| | UNTREATED | | | | |
|---|---|---|---|---|---|
| | **OD 1** | **OD 2** | **AVE** | **SD** | **%** |
| **<1H** | 0.14 | 0.13 | 0.135 | 0.007 | 100 |
| **24H RT** | 0.085 | 0.07 | 0.078 | 0.011 | **57** |
| **24H 4°C** | 0.075 | 0.06 | 0.068 | 0.011 | **50** |
| | **L-GLUTATHIONE (REDUCED) 5mM** | | | | |
| | **OD 1** | **OD 2** | **AVE** | **SD** | **%** |
| **<1H** | 0.117 | 0.13 | 0.124 | 0.009 | 100 |
| **24H RT** | 0.124 | 0.126 | 0.125 | 0.001 | 101 |
| **24H 4°C** | 0.106 | 0.142 | 0.124 | 0.025 | 100 |
| | **EGTA (5mM)** | | | | |
| | **OD 1** | **OD 2** | **AVE** | **SD** | **%** |
| **<1H** | 0.127 | 0.135 | 0.131 | 0.006 | 100 |
| **24H RT** | 0.118 | 0.102 | 0.110 | 0.011 | **84** |
| **24H 4°C** | 0.09 | 0.092 | 0.091 | 0.001 | **69** |

A

| SCRAPIE SHEEP #3 | | | | | |
|---|---|---|---|---|---|
| | UNTREATED | | | | |
| | **OD 1** | **OD 2** | **AVE** | **SD** | **%** |
| **<1H** | 0.34 | 0.355 | 0.348 | 0.011 | 100 |
| **24H RT** | 0.32 | 0.289 | 0.305 | 0.022 | **88** |
| **24H** | 0.269 | 0.273 | 0.271 | 0.003 | **78** |
| | **L-GLUTATHIONE (REDUCED) 5mM** | | | | |
| | **OD 1** | **OD 2** | **AVE** | **SD** | **%** |
| **<1H** | 0.412 | 0.359 | 0.386 | 0.037 | 100 |
| **24H RT** | 0.366 | 0.406 | 0.386 | 0.028 | 100 |
| **24H** | 0.571 | 0.333 | 0.452 | 0.168 | 117 |

B

| SCRAPIE SHEEP #3 | | | | | |
|---|---|---|---|---|---|
| | UNTREATED | | | | |
| | OD 1 | OD 2 | AVE | SD | % |
| <1H | 0.105 | 0.096 | 0.101 | 0.006 | 100 |
| 24H RT | 0.127 | 0.109 | 0.118 | 0.013 | 117 |
| 24H | 0.093 | 0.102 | 0.098 | 0.006 | 97 |
| | L-GLUTATHIONE (REDUCED) 5mM | | | | |
| | OD 1 | OD 2 | AVE | SD | % |
| <1H | 0.117 | 0.108 | 0.113 | 0.006 | 100 |
| 24H RT | 0.092 | 0.112 | 0.102 | 0.014 | 90 |
| 24H | 0.111 | 0.118 | 0.115 | 0.005 | 101 |

A

B

| TREATMENT | PROCESSING TIME | OD (AVE) | % TOTAL SIGNAL FROM IMMEDIATE PROCESSING WITHOUT TREATMENT | % LOSS |
|---|---|---|---|---|
| NONE | IMMEDIATE | 0.25 | 100 | 0 |
| NONE | AFTER OVERNIGHT@RT | 0.056 | 22.4 | 77.6 |
| L-GLUT (RED) | IMMEDIATE | 0.29 | 116 | 0 |
| L-GLUT (RED) | AFTER OVERNIGHT@RT | 0.229 | 91.6 | 8.4 |
| L-GLUT (OXI) | IMMEDIATE | NOT DONE | BUFFY COAT LOST DURING PROCESSING | N / A |
| L-GLUT (OXI) | AFTER OVERNIGHT@RT | 0.087 | 34.8 | 65.2 |
| EGTA | IMMEDIATE | 0.252 | 100.8 | 0 |
| EGTA | AFTER OVERNIGHT@RT | 0.114 | 45.6 | 54.4 |

DETECTION OF ANALYTES PRESENT IN EXOSOMES

BACKGROUND OF THE INVENTION

PrPsc can be detected in buffy coat fractions of blood. Detection of PrPsc from buffy coat fractions provides a way to concentrate the sample and to remove interfering substances in plasma. However, the magnitude of detection is inversely related to the age of the blood sample at time of processing. That is, "aged" buffy coat samples retain less signal than matched buffy coat samples that are processed immediately. Therefore, sensitive and specific methods of detection of PrPsc in stored biological samples are needed in the art.

SUMMARY OF THE INVENTION

One embodiment of the invention provides methods for preparing a biological sample comprising leukocytes for detection of analytes associated with exosomes. The methods comprise collecting a biological sample having leukocytes from a subject and adding an inhibitor of N-SMase to the sample. The inhibitor of N-SMase can be glutathione (reduced form), spiroepoxide, N,N'-Bis [4-(4,5-dihydro-1H-imidazol-2-yl)phenyl]-3,3'-p-phenylene-bis-acrylamide dihydrochloride, or ethylene glycol tetraacetic acid (EGTA). The inhibitor can be added at a concentration of about 5 to about 75 mM. The inhibitor of N-SMase can be added to the sample up to 1 hour after collection of the sample. The subject can be a human, cervid, caprine, bovine, ovine, rodent, mink, feline or a primate. The sample comprising leukocytes can be a whole blood sample, a blood fraction containing leukocytes, a blood fraction containing peripheral blood mononuclear cells, tissue, or body fluids containing cellular fractions. The analyte can be PrPsc, a virus, or an exosome marker. The biological sample can be purified or fractionated before or after the addition of the inhibitor of N-SMase to the sample.

Another embodiment of the invention provides methods of detection of an analyte associated with exosomes. The methods comprise collecting a biological sample comprising leukocytes from a subject; adding an inhibitor of N-SMase to the sample; optionally storing the sample for a period of time; assaying the sample for the presence of the analyte. The inhibitor of N-SMase can be glutathione (reduced form), spiroepoxide, N,N'-Bis [4-(4,5-dihydro-1H-imidazol-2-yl) phenyl]-3,3'-p-phenylene-bis-acrylamide dihydrochloride, or ethylene glycol tetraacetic acid (EGTA). The inhibitor can be added at a concentration of about 5 to about 75 mM. The subject can be a human, cervid, caprine, bovine, ovine, rodent, mink, feline or a primate. The sample comprising leukocytes can be a whole blood sample, a blood fraction containing leukocytes, a blood fraction containing peripheral blood mononuclear cells, tissue, or body fluids containing cellular fractions. The analyte can be PrPsc, a virus, or an exosome marker. The biological sample can be purified or fractionated before or after the addition of the inhibitor of N-SMase to the sample.

Therefore, the invention provides improved methods of detection of analytes associated with exosomes in samples comprising leukocytes, including samples that stored over time.

DETAILED DESCRIPTION OF THE INVENTION

Figure 1:
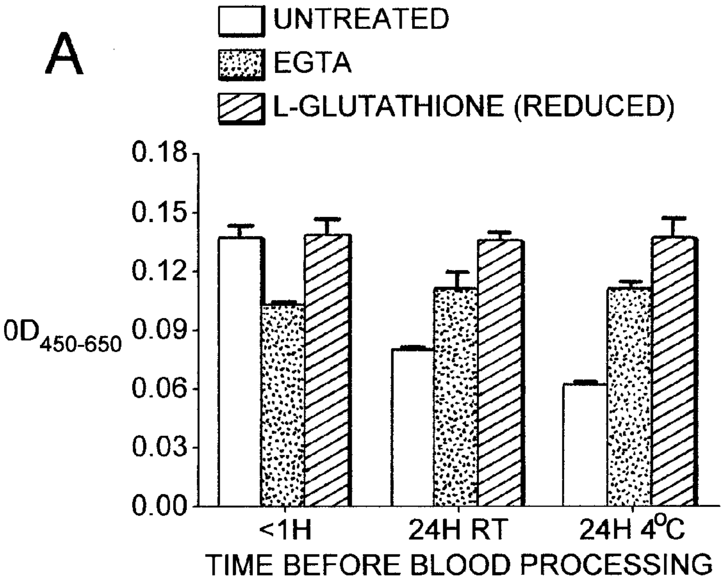
FIG. 1A-B shows the effect of L-glutathione (reduced) and EGTA on the PrPsc signal obtained from the buffy coat of pre-clinical scrapie sheep when added to whole blood and the sample are stored for less than an hour or for 24 h.

As used herein, the singular forms "a," "an", and "the" include plural referents unless the context clearly dictates otherwise.

The detection of PrPsc in blood from antemortem transmissible spongiform encephalopathies (TSE) samples is problematic. The detection signal for PrPsc is lost partially or fully when PrPsc is present in plasma. For example, a full PrPsc detection signal (if any) cannot be obtained from plasma samples supplemented with PrPsc from brain homogenates of scrapie sheep. However, when buffy coat fractions of blood samples are used to detect PrPsc, the magnitude of detection is inversely related to the age of the blood sample at the time of detection. Therefore, samples must be assayed immediately after collection to obtain sensitive and specific results.

PrPsc can be found in exosomes, which are membrane-bounded subcellular compartments found in several cell types, including neurons and cells of the immune system that are involved in antigen presentation. These bilayer vesicles should not be confused with ribonuclease complexes capable of degrading RNAs, which can also be called exosomes. Neutral sphingomyelinase (N-SMase) activity is required for cells to release exosomes into their environment. It has now been discovered that treatment of biological samples with inhibitors of N-SMase activity prevents the loss of PrPsc signal that occurs in the time interval between sample collection and signal detection. For example, glutathione, a potent inhibitor of N-SMase, can preserve the detection signal in buffy coat fractions of blood samples from scrapie animals that were processed 24 hours post-collection. See Examples. Therefore, inhibitors of N-SMase can be added to the sample at or around the time of sample collection to prevent shedding of analytes from cells via exosomes, thereby preserving the ability to detect PrPsc or other analytes in samples after collection of the samples.

One embodiment of the invention provides methods for preparing or preserving a biological sample for detection of analytes present in or associated with exosomes or leukocytes. Analytes associated with exosomes or leukocytes are analytes that are present within exosomes or leukocytes or are part of the exosome or leukocytes (i.e., molecules that make up the exosome or leukocyte or are covalently or non-covalently attached to the exosome or leukocyte). The methods comprise collecting a biological sample comprising leukocytes from a subject and adding an inhibitor of N-SMase to the sample. The biological sample can be collected from any mammal, e.g., humans, cervids, caprines, bovines, ovines, rodents, mink, felines, or primates. The biological sample can be, e.g., a whole blood sample, a blood fraction containing leukocytes (e.g., a buffy coat fraction or a population of peripheral blood mononuclear cells (which can be isolated using, e.g., Ficoll-Hypaque techniques), tissue, and body fluids containing cellular fractions (e.g., cerebral spinal fluid, lymph fluid, whole blood, and urine). An inhibitor can be added to the biological sample itself, or can be added to a purified portion or fraction of the sample. For example an inhibitor of N-SMase can be added to whole blood samples (which can then be fractionated or purified) or a buffy coat fraction of the whole blood sample.

The inhibitor of N-SMase can be, for example, L-glutathione (reduced form), spiroepoxide, N,N'-Bis [4-(4,5-dihydro-1H-imidazol-2-yl)phenyl]-3,3'-p-phenylene-bis-acrylamide dihydrochloride (GW4869; Calbiochem, San Diego Calif.), ethylene glycol tetraacetic acid (EGTA), or combinations thereof; however, any inhibitor of N-SMase can be used in the methods of the invention. The inhibitor can be added at a concentration of about 1, 2, 3, 4, 5, 10, 20, 30, 40, 50, 60, 70, 75, 80, 90, 100, 125, 150 mM (or any range or value between about 1 mM and 150 mM, e.g., about 5 mM to about 20 mM or about 5 mM to about 75 mM). In one embodiment of the invention the inhibitor of N-SMase is added to the biological sample immediately after collection of the sample, but the inhibitor of N-SMase can be added to the sample at about 2 hours, 1.5 hours, 1 hour, 50 minutes, 40 minutes, 30 minutes, 20 minutes, 10 minutes, 5 minutes, 4 minutes, 3 minutes, 2 minutes, 1 minute (or any range or value between about 2 hours and 1 minute, e.g. about 1 hour to about 1 minute) or less after collection of the sample. The sample can be fractionated or purified before or after addition of the N-SMase inhibitor.

The analyte to be assayed can be, e.g., PrPsc, viruses that can be found in leukocytes or exosomes (e.g., all major classes of exogenous vertebrate retroviruses, including the alpharetroviruses (e.g., avian myeloblastosis virus and avian leukosis virus), betaretroviruses (e.g., mouse mammary tumor virus), gammaretroviruses (e.g., murine leukemia virus), deltaretroviruses (e.g., human T-lymphotrophic virus (HTLV-1) and bovine leukemia virus), lentiviruses (e.g., simian immunodeficiency virus, HIV, and Maedi-Visna virus), and spumaviruses), or any other analyte normally associated with an exosome or leukocyte, such as an endogenous exosome markers, e.g., annexins, acetylcholinesterase, CD24, flotillin, Rab, integrins, hsp70, Hsc73, Hsc90, subunits of trimeric G proteins, Tsg101, tetraspanins (e.g., CD9, CD63, CD81, CD82, and CD151), and a variety of GPI (glycerol-phosphatidyl inositol)-anchored proteins, among others.

Infectious prions (PrPsc) are conformationally modified forms of the normal cellular (PrPc) prion protein. The modification of PrPc to PrPsc can lead to the development of transmissible spongiform encephalopathies (TSEs), wherein PrPsc accumulates in the central nervous system and causes neuropathologic changes and neurological dysfunction. TSEs include scrapie, which affects sheep and goats; bovine spongiform encephalopathy (BSE), which affects cattle; transmissible mink encephalopathy; feline spongiform encephalopathy; and chronic wasting disease (CWD) of mule deer, white-tailed deer, black-tailed deer and elk. In humans, TSE diseases include kuru, Creutzfeldt-Jakob disease (CJD), Gerstmann-Straussler-Scheinker Syndrome (GSS), fatal insomnia and variant Creutzfeldt-Jakob disease (vCJD).

One embodiment of the invention provides improved methods for detection of an analyte associated with exosomes or leukocytes comprising collecting a biological sample comprising leukocytes from a subject, adding an inhibitor of N-SMase to the sample, optionally storing the sample for a period of time, and assaying the sample for the presence of the analyte. The sample can be stored for 5 minutes, 30 minutes, 1 hour, 2 hours, 5 hours 10 hours, 24 hours, 48 hours, 72 hours, a week, or longer. The sample can be stored at any temperature, e.g., −70, −20, 0, 4, or 20 degrees Celsius or at room temperature.

Analytes can be detected using any immunological assay methods known in the art including, e.g., enzyme immunoassays, western blot assays, competitive binding assays, radioimmunoassays, immunofluorescent assays, immuno-precipitation assays, chemiluminescent assays, immunohistochemical assays, dot blots, slot blots, ELISA assays, fluorescence-activated cell analyses, PCR assays, protein misfolding cyclic amplification (PMCA) assays, quaking induced conversion (QUIC) assays, and nucleic acid detection assays. The assays can be quantitative or semi-quantitative.

For example, where PrPsc is an analyte, detection can be done using an antigen-capture enzyme immunoassay such as IDEXX HerdChek® Bovine Spongiform Encephalopathy-Scrapie Antigen Test Kit. Where a virus is an analyte, immunological or nucleic acid assays specific for that virus can be used. Assays for endogenous exosome markers and analytes associated with leukocytes are well known in the art.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms “comprising”, “consisting essentially of”, and “consisting of” may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims. In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

L-glutathione, an inhibitor of neutral sphingomyelinase (N-SMase), as well as EGTA, a calcium chelator was used to preserve the PrPsc signal present in buffy coat preparations from scrapie blood. The L-glutathione was added directly to the blood and stored under various conditions. The PrPsc signal in buffy coat preparations was measured using the IDEXX HerdChek® Bovine Spongiform Encephalopathy-Scrapie Antigen Test Kit (“the IDEXX BSE/scrapie kit”).

L-glutathione (reduced) or EGTA was added at the time of collection to whole blood at 5 mM final concentration on the PrPsc signal of buffy coat isolated from whole blood from ARQ/ARQ scrapie sheep and submitted to various storage conditions prior to processing. FIG. 1 demonstrates that L-glutathione (reduced) and EGTA preserve the PrPsc signal from the buffy coat of pre-clinical scrapie sheep #1 (ARQ/ARQ) when added to whole blood and stored for 24 h. FIG. 1A shows the Optical Density (OD) signals from scrapie blood leukocytes ($1\times10^7$ cells/100μL) processed immediately or after storage at 4° C. or room temperature (20-25° C.) for 24 hours. FIG. 1B shows tabular data of the same experiment showing percentage change analysis. Percentage of samples processed after 24 h represents the residual signal relative to the signal of the sample processed immediately, which is defined as 100% signal for each treatment condition. Bolded numbers indicate >10% decrease in signal, while underlined numbers indicate little or no significant change. The PrPsc signal in buffy coat preparations was measured using the IDEXX BSE/scrapie kit.

Figure 2:
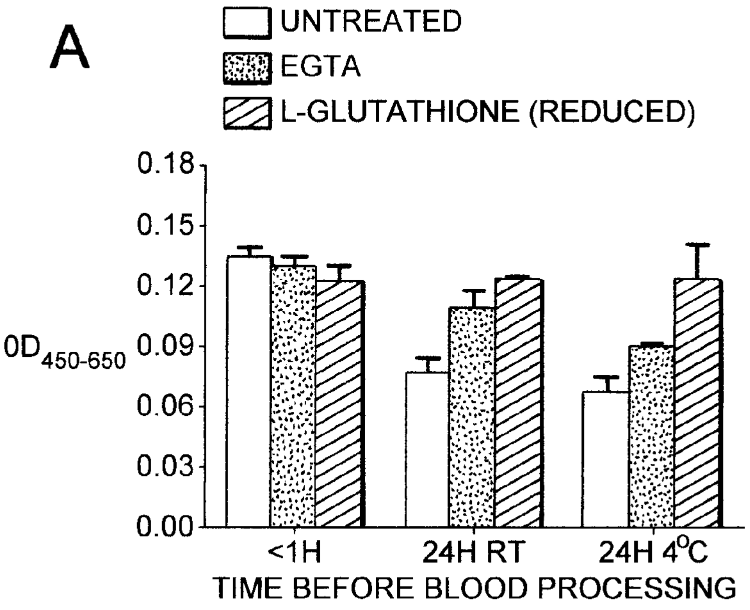
FIG. 2A-B shows the effect of L-glutathione (reduced) and EGTA on the PrPsc signal obtained from the buffy coat of pre-clinical scrapie sheep when added to whole blood and the sample are stored for less than an hour or for 24 h.

A second trial to test the effect of adding L-glutathione (reduced) or EGTA at time of collection to whole blood at 5 mM final concentration on the PrPsc signal of buffy coat isolated from whole blood from ARQ/ARQ scrapie sheep and submitted to various storage conditions prior to processing is shown in FIG. 2. L-glutathione (reduced) and EGTA preserve the PrPsc signal from the buffy coat of pre-clinical scrapie sheep #2 (ARQ/ARQ) when added to whole blood and stored for 24 h. FIG. 2A shows the OD signals from scrapie blood leukocytes ($1\times10^7$ cells/100μL) processed immediately or after storage at 4° C. or room temperature (20-25° C.) for 24 hours. FIG. 2B shows tabular data of the same experiment showing percentage change analysis. Percentage of samples processed after 24 h represents the residual signal relative to the signal of the sample processed immediately, which is defined as 100% signal for each treatment condition. Bold numbers indicate >10% decrease in signal, while underlined numbers indicate little or no significant change. The PrPsc signal in buffy coat preparations was measured using the IDEXX BSE/scrapie kit.

Figure 3:
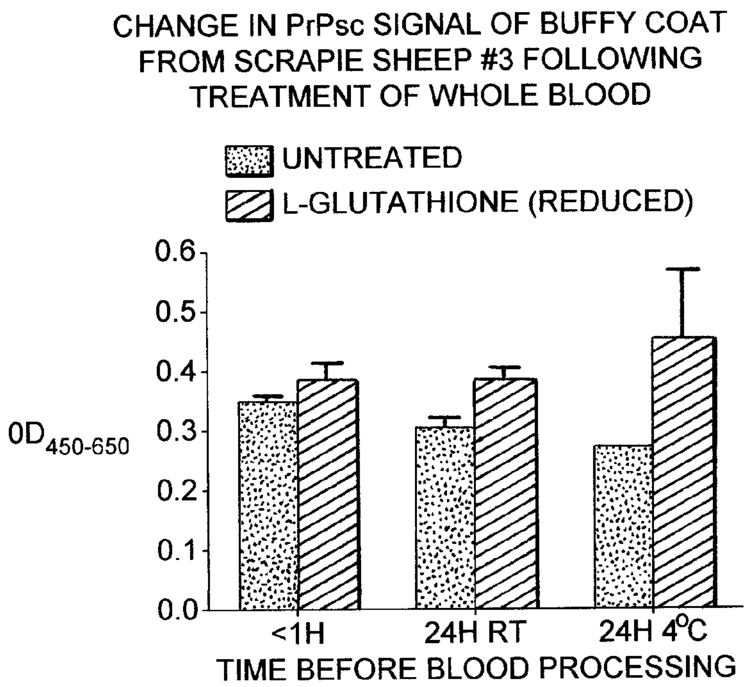
FIG. 3A-B shows the effect of adding L-glutathione (reduced) or EGTA at time of collection to whole blood from normal and scrapie sheep and submitted to various storage conditions prior to processing.
Figure 3:
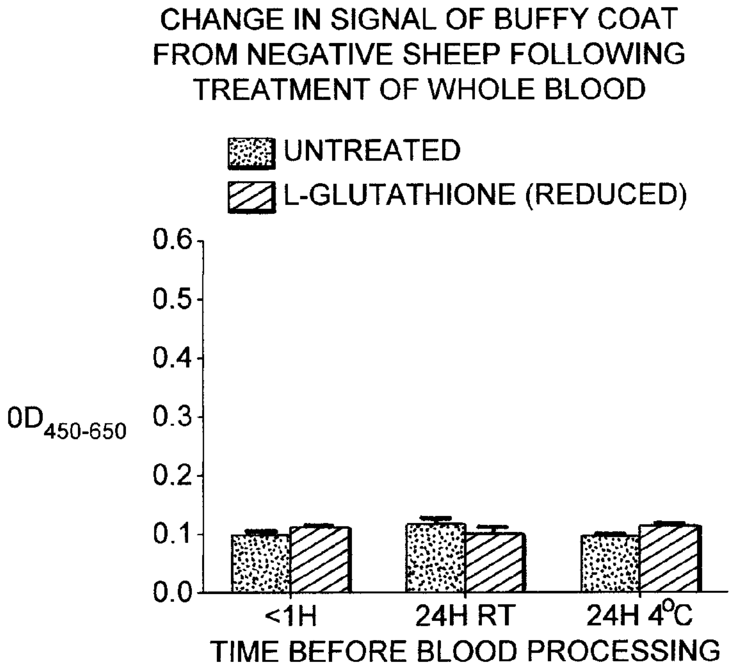

The effect of adding L-glutathione (reduced) or EGTA at time of collection to whole blood from normal and ARQ/ARQ scrapie sheep and submitted to various storage conditions prior to processing is shown in FIG. 3. FIG. 3 shows the effect of overnight incubation of whole blood from scrapie (ARQ/ARQ) and normal sheep with L-glutathione (reduced). FIG. 3A shows OD signals from scrapie blood leukocytes ($1\times10^7$ cells/100μL) processed immediately or after storage at 4° C. or room temperature (20-25° C.) for 24 hours. FIG. 3B shows OD signals from normal blood leukocytes ($1\times10^7$ cells/100μL) processed immediately or after storage at 4° C. or room temperature (20-25° C.) for 24 hours. Tabular data of the same experiment showing percentage change analysis. Percentage of samples processed after 24 h represents the residual signal relative to the signal of the sample processed immediately, which is defined as 100% signal for each treatment condition. Bold numbers indicate >10% decrease in signal, while underlined numbers indicate little or no significant change. The PrPsc signal in buffy coat preparations was measured using the IDEXX BSE/scrapie kit.

Figure 4:
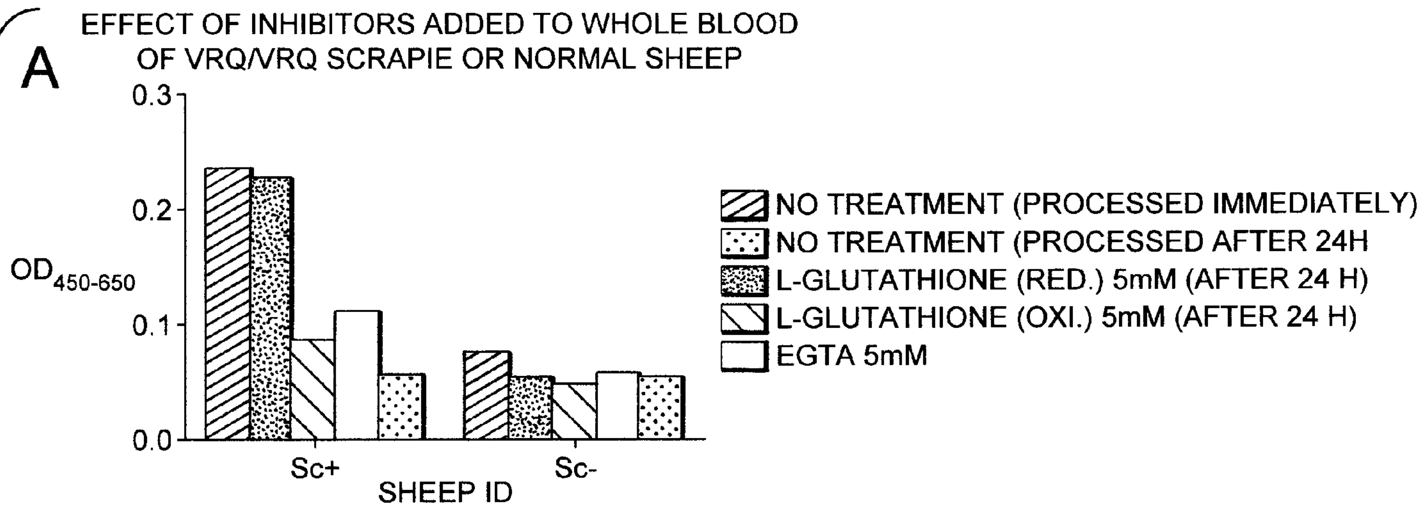
FIG. 4A-B shows the evaluation of EGTA and either the oxidized or reduced form of L-glutathione at time of collection of whole blood from normal and scrapie sheep submitted to 24 h storage conditions at room temperature prior to processing, or processed immediately.

FIG. 4 shows the evaluation of EGTA and either the oxidized or reduced form of L-glutathione at time of collection of whole blood from normal and scrapie sheep (VRQ/VRQ) submitted to 24 h storage condition at room temperature prior to processing, or processed immediately. FIG. 4 shows the effect of L-glutathione (reduced) and EGTA on blood from VRQ/VRQ scrapie and normal sheep. FIG. 4A shows OD signals from scrapie and normal blood leukocytes ($1\times10^7$ cells/100 μL) processed immediately or after storage at room temperature (20-25° C.) for 24 hours. FIG. 4B shows tabular data of the same experiment showing percentage loss of signal relative to the signal of the sample processed immediately, which is defined as 100% signal for each treatment condition (also shown as 0% loss). Note the lack of effect of the oxidized L-glutathione compared to the reduced form. For the oxidized glutathione, the percentage loss was calculated relative to the untreated sample processed immediately.

Therefore, the reduced form of L-glutathione and EGTA allow for the preservation of the PrPsc harbored in the buffy coat of blood from scrapie sheep of both ARQ/ARQ and VRQ/VRQ genotype backgrounds after these additives were incorporated in the blood and stored for at least 24 h.

We claim:

1. A method for preparing a biological sample comprising leukocytes for detection of analytes associated with exosomes comprising:

(a) collecting a biological sample comprising leukocytes from a subject;

(b) adding an inhibitor of N-SMase to the sample.

2. The method of claim 1 wherein the inhibitor of N-SMase is a reduced form of glutathione, spiroepoxide, N,N'-Bis[4-(4,5-dihydro-1 H-imidazol-2-yl)phenyl]-3,3'-p-phenylene-bis-acrylamide dihydrochloride, or ethylene glycol tetraacetic acid (EGTA).

3. The method of claim 1, wherein the inhibitor is added at a concentration of about 5 to about 75 mM.

4. The method of claim 1, wherein the inhibitor of N-SMase is added to the sample up to 1 hour after collection of the sample.

5. The method of claim 1, wherein the subject is a human, cervid, caprine, bovine, ovine, rodent, mink, feline or a primate.

6. The method of claim 1, wherein the sample comprising leukocytes is a whole blood sample, a blood fraction containing leukocytes, a blood fraction containing peripheral blood mononuclear cells, tissue, or body fluids containing cellular fractions.

7. The method of claim 1, wherein the analyte is PrPsc, a virus, or an exosome marker.

8. The method of claim 1, wherein the biological sample is purified or fractionated before or after the addition of the inhibitor of N-SMase to the sample.

9. A method of detection of an analyte associated with exosomes comprising (a) collecting a biological sample comprising leukocytes from a subject;

(b) adding an inhibitor of N-SMase to the sample;

(c) optionally storing the sample for a period of time;

(d) assaying the sample for the presence of the analyte.

10. The method of claim 9, wherein the inhibitor of N-SMase is a reduced form of glutathione, spiroepoxide, N,N'-Bis[4-(4,5-dihydro-1H-imidazol-2-yl)phenyl]-3,3'-p-phenylene-bis-acrylamide dihydrochloride, or ethylene glycol tetraacetic acid (EGTA).

11. The method of claim 9, wherein the inhibitor is added at a concentration of about 5 to about 75 mM.

12. The method of claim 9, wherein the subject is a human, cervid, caprine, bovine, ovine, rodent, mink, feline or a primate.

13. The method of claim 9, wherein the sample comprising leukocytes is a whole blood sample, a blood fraction containing leukocytes, a blood fraction containing peripheral blood mononuclear cells, tissue, or body fluids containing cellular fractions.

14. The method of claim 9, wherein the analyte is PrPsc, a virus, or an exosome marker.

15. The method of claim 9, wherein the biological sample is purified or fractionated before or after the addition of the inhibitor of N-SMase to the sample.

* * * * *